United States Patent [19]

Gallacher

[11] Patent Number: 4,615,972

[45] Date of Patent: Oct. 7, 1986

[54] STABILIZATION OF INDICATORS FOR DETECTING ENZYME ACTIVITY

[75] Inventor: James J. Gallacher, Irving, Tex.

[73] Assignee: Immuno Concepts, Inc., Sacramento, Calif.

[21] Appl. No.: 548,623

[22] Filed: Nov. 4, 1983

[51] Int. Cl.⁴ ............................................. C12Q 1/28
[52] U.S. Cl. ......................................... 435/28; 436/8; 436/166; 436/176; 436/904; 436/512; 436/513; 435/4; 435/7
[58] Field of Search ................. 435/7, 28; 436/8, 166, 436/176, 904, 529; 422/56, 57, 61

[56] References Cited

U.S. PATENT DOCUMENTS

| | | | |
|---|---|---|---|
| 3,843,324 | 10/1974 | Edelman et al. | 436/529 |
| 3,853,471 | 12/1974 | Rittersdorf et al. | 436/66 |
| 3,950,133 | 4/1976 | Monte et al. | 436/166 |
| 4,017,261 | 4/1977 | Svoboda et al. | 422/56 |
| 4,071,318 | 1/1978 | Lam | 436/166 |
| 4,143,080 | 3/1979 | Harders et al. | 436/66 |
| 4,169,012 | 9/1979 | Dawson et al. | 435/7 |
| 4,228,240 | 10/1980 | Dawson et al. | 435/188 |
| 4,252,896 | 2/1981 | Shaffar | 435/7 |
| 4,269,938 | 5/1981 | Frank | 422/56 |
| 4,312,834 | 1/1982 | Vogel et al. | 436/66 |
| 4,336,243 | 12/1982 | Rupchock et al. | 424/28 |
| 4,340,395 | 7/1982 | Magers et al. | 436/66 |
| 4,372,746 | 2/1983 | Habenstein | 436/66 |
| 4,380,585 | 4/1983 | Magers et al. | 436/66 |

OTHER PUBLICATIONS

Histological and Histochemical Methods by J. A. Kiernan, Dept. of Anatomy, The University of Western Ontario, London, Ontario Canada, Mar. 1982, pp. 233-236.
Votila et al., Journal of Immunological Methods, 1981, vol. 42, pp. 11-15.

*Primary Examiner*—Sam Rosen
*Assistant Examiner*—William J. Herald
*Attorney, Agent, or Firm*—Fulwider, Patton, Rieber, Lee & Utecht

[57] ABSTRACT

A stabilized indicator powder for use in assays to detect the presence of peroxidase or other peroxidatively active substances, wherein the indicator is stabilized by being combined with a water soluble polymer. As a dry powder, the indicator retains its reactivity for at least several months. The powder readily dissolves in an aqueous medium and as a solution retains its reactivity for a period of weeks, even in the presence of peroxide.

24 Claims, No Drawings

STABILIZATION OF INDICATORS FOR DETECTING ENZYME ACTIVITY

BACKGROUND OF THE INVENTION

The present invention relates generally to the field of biochemical assays for the presence of peroxidase or other peroxidatively active substances. More specifically, it relates to a stabilizer useful both to stabilize and to solubilize an indicator for subsequent use to detect peroxidase activity.

The enzyme peroxidase acts to catalyze the redox reaction transfer of hydrogen from a hydrogen donor to a hydrogen acceptor. The hydrogen donor, or indicator, may be a chromogen which exhibits color in the oxidized state, so that peroxidase activity may be detected by monitoring color change. Alternatively, the hydrogen donor may be chosen from the class of indicators which emit light or exhibit other detectable features in the oxidized state. The hydrogen acceptor is typically hydrogen peroxide or a related compound such as methyhydroperoxide or ethylhydroperoxide.

The detection of peroxidase and peroxidase-like activity has utility in a variety of medically related fields. In the area of cytochemistry, for example, the detection of such activity can be used to identify and monitor certain cell types. Peroxidatively active substances are present in a restricted set of cell types including myeloid leukocytes and granulcytes, erythrocytes, and certain neurons and secretory cells. Mitotic cells also exhibit peroxidase-like activity. Assays sensitive to peroxidase activity can be used for certain medical determinations based on cytological condition.

Furthermore, in recent years assays based on peroxidase activity have provided a powerful tool in the immunochemical field, to aid in the detection of certain types of proteins, for example. Peroxidase is readily extractable and available in quantity from horseradish root. An antibody specific to a particular protein may be conjugated with the extracted peroxidase. After allowing the antibody to react with the protein antigen, the protein-antibody-peroxidase complex may be detected by providing appropriate hydrogen donors and acceptors and monitoring the redox reaction. Such methodology has been used in assays for a wide variety of ligands including proteins, peptides, carbohydrates and any other immunologically active substance.

In one such approach, antinuclear antibodies may be detected in human serum through the use of the peroxidase redox reaction. HEP-2 cells are fixed onto a slide, and then the cells are contacted with a serum which may contain antinuclear antibodies. If present in the serum, the antinuclear antibodies will react with the HEP-2 cells. After washing off the excess serum, the HEP-2 cells bonded with antinuclear antibodies are then further reacted with a solution containing antihuman IgG antibodies conjugated with peroxidase enzyme. The antihuman IgG antibodies are specific to any antinuclear antibodies bonded to the HEP-2 cells so that the peroxidase enzyme will be present on the slide after washing excess solution away only if antinuclear antibodies were present in the serum. Finally, the reacted cells fixed to the slide are contacted with a chromogenic indicator in a buffered aqueous solution which also contains peroxide, so that the peroxidase-catalyzed redox reaction may occur. By this procedure, the HEP-2 cells will be colored only to the extent that antinuclear antibodies were present in the serum reacted with the HEP-2 cells. With relatively minor modifications to the preparation of the slide and attached cells, other antigen reactions, such as for DNA or chlomydiae may be detected.

In another entirely different technique, "dip-and-read" type reagent bearing strips are used to detect peroxidase activity. These strips comprise a porous insoluble matrix strip first impregnated with a suitable hydrogen donor and acceptor and then dried. When immersed in a solution containing peroxidase, the indicator is oxidized, typically containing peroxidase, the indicator is oxidized, typically changing color. The "dip-and-read" technique has the advantage of ease of usage but obviously cannot be used in tests involving cell coloring by wet chemistry on a microscope slide.

A continuing problem with the peroxidase methodology for both the wet chemical approach and the dip-and-read strip approach is the gradual but spontaneous oxidation of the indicator. Such deterioration proceeds even more readily in an aqueous or peroxide containing medium. So rapid is this deterioration that reagent solutions must be prepared fresh within about a day prior to use, resulting in an excessive waste of valuable preparation time and costly reagents if all of each batch of reagent is not utilized.

Additionally, certain frequently used and desirable indicators, notably 4-chloro-1-napthol and 3-amino-9-ethylcarbazole, are insoluble in water. Accordingly, these types of compounds must first be dissolved in an organic solvent such as alcohol or dimethylsulfoxide to effect solubilization of the indicator before further mixing with an aqueous medium. These reagent solutions must also be prepared immediately prior to use as the indicator may precipitate out of solution upon standing.

Methods have been developed to inhibit spontaneous oxidation of the indicator on a dip-and-read strip. For example, the physical separation of the reagents may retard deterioration. Such separation may be effected by successive impregnation of the test strip with an indicator solution, a polyvinylmethylacylamide solution and a peroxide solution, with drying between each step. The polyvinylmethacrylamide forms a protective colloid, effectively separating the two reagents by a physical wall or barrier. Similarly, the peroxide may be encapsulated within a colloidal material such as gelatin which also acts as a physical barrier. In dip-and-read strips to which only an indicator is bound, certain lower alkyl or alkylene derivatives or monoalcohols have the effect of increasing the indicator's stability.

While applicable to the dip-and-read technique, such a physical barrier stabilization approach is obviously inappropriate for use in wet chemical methods. Reagent instability and insolubility continue to present serious limitations on the convenience and desirability of wet chemical peroxidase-related assay techniques.

The limitations are particularly apparent when tests such as the antinuclear antibody test described above are to be performed in a doctor's office, a field clinic, or by relatively unskilled personnel. Where the testing is to be performed at a location where the demand for testing is so low that only one or a few test are performed each day, a major portion of the costly indicator reagent solution may be discarded because the spontaneous oxidation renders the solution unreliable after short storage periods. When relatively unskilled persons are involved in the testing, the need to dissolve the indicator in an organic liquid prior to mixing with an aqueous solution may be overly complex, and may result in mixing errors which can invalidate the test procedure. Further, if peroxide must be added at the time of use because the indicator solution is unstable in the presence of peroxide, further mixing errors may result. Thus, it would be highly desirable to have an indicator which is readily soluble in aqueous solution and is stable for a period of time, even in the presence of peroxide. Such a solution could be prepared by one person and then used without further modification by a technician to prepare specimens for analysis.

Accordingly, there exists a need for a stabilized indicator/peroxide solution which may be prepared from a stable reagent which is soluble in water. Ideally, such a solution would be stable for an extended period of time, even in the presence of peroxide. The present invention fulfills this need, and further provides related advantages.

SUMMARY OF THE INVENTION

The present invention provides an improved powdered indicator which resists spontaneous oxidation for use in detecting peroxidase activity. A further aspect of the invention is that the indicator is readily dissolved in an aqueous medium and remains stable for a period of weeks, even in the presence of peroxide. The reagent may be maintained in a laboratory over long periods as a dry powder, and then dissolved in an aqueous solution which may contain peroxide. The solution is stable during storage and may then be used with results comparable to freshly prepared solution. The unnecessary waste of costly reagents or personnel time is thereby avoided since frequent disposal of excess solution is not necessary.

In accordance with the invention, an indicator is combined with a stabilizer substance to produce a stabilized indicator powder. Preferred stabilizers are solid water soluble polymers. This indicator powder may be maintained at room temperature in a dry state or may be dissolved in an aqueous medium. If desired, an oxidizing agent such as peroxide may be added to the solution in order to have a ready-to-use, stabilized solution. Even with the addition of peroxide, the solution is stable for at least several weeks. Contact of the solution with peroxidase catalyzes the reaction whereby the indicator is oxidized, producing a detectable change such as a color change. Tests have shown that the results obtained using stabilized solutions maintained for several weeks are comparable to those employing freshly made solutions, and provide acceptable indications of peroxidase activity.

In a preferred embodiment, a solid chromogenic indicator and a solid water-soluble polymer are mixed with a paddle and then ground with a mortar and pestle or, more typically, with a ball mill. Preferably, the chromogenic indicator is 4-chloro-1-naphthol and the polymer is polyethylene glycol. The ratio of the former to the latter is not critical but is preferably in the range of about 1 to 250 parts by weight. The resulting powder is stable for a period of at least several months in the dry state.

To prepare an indicator solution for a peroxidase assay, the stabilized powder is added to an aqueous medium and stirred to dissolve. Preferably, about 3 gm. of powder is dissolved in 100 ml of aqueous medium, but again the ratio is not critical. The resulting solution may be stored as it is or with the addition of peroxide for at least several weeks before use, without significant loss of effectiveness.

It will be appreciated from the foregoing that the present invention constitutes a significant advance in the field of assay procedures. The process of the present invention allows reagents to be prepared and maintained for an extended period of time, resulting in a conservation of valuable materials and manpower. Further, by promoting solubilization of the indicator as well, the stabilizer reduces the chances of errors in preparation and also reduces preparation time, and prevents the indicator from precipitating out of solution. A powdered reagent which is stable for some months can be easily shipped throughout the world. Analytical laboratories can maintain the reactive compound on their shelves. Further, the stabilized solutions need only be prepared every few weeks, rather than daily, thereby decreasing costs and increasing efficiency.

Other features and advantages of the present invention will become apparent from the following detailed description which illustrates, by way of example, the principles of the invention.

DETAILED DESCRIPTION OF THE PREFERRED EMBODIMENT

A variety of indicators well known in the art are oxidized to colored forms in the presence of peroxide, and peroxidase or a peroxidase-like substance. Among the compounds that are frequently used are benzidine, dimethylbenezidine, o-phenylenediamine, p-phenylenediamine, 4-chloro-1-naphthol and 3-amino-9-ethylcarbazole. All are susceptible to spontaneous oxidation in aqueous solution, which ordinarily necessitates preparing each solution immediately prior to use.

In the prior methodology, an indicator is added to and mixed with an aqueous solution. Certain indicators, notably 4-chloro-1-naphthol and 3-amino-9-ethylcarbazole, are not readily soluble in water. These must be first dissolved in an organic solvent such as alcohol or dimethylsulfoxide and then dissolved in an aqueous solution. Once a fully dissolved solution is prepared, it must be used within a day or so in an assay procedure, or spontaneous oxidation will reduce its effectiveness and render the assay results suspect. Peroxide is added to the solution immediately prior to use.

In accordance with the present invention, a stabilized indicator powder for subsequent use in detecting peroxidase activity is prepared by combining an indicator and a stabilizer. The resulting material is then dissolved in an aqueous medium, which may or may not contain peroxide.

To prepare the stabilized indicator powder, an indicator is combined with a water soluble polymer such as polyethylene glycol, polyethyleneoxide or polyvinylpyrrolidone and derivatives thereof, by mixing and grinding. To prepare the stabilized indicator powder, the two compounds are first mixed with a paddle and then ground together, either with a mortar and pestle or a ball mill for thirty minutes in the cold (4°–8° C). The amount of the indicator combined with the stabilizer is not critical, although a ratio of about 1 part of indicator to about 250 parts of stabilizer, by weight, has been found effective.

It is sometimes noticed that the solid indicator and the stabilizer do not mix uniformly, particularly when large quantities are mixed together. An even distribution can be obtained by first mixing the indicator with a salt such as sodium chloride, and then combining this mixture with the stabilizer as described previously. Sodium chloride is preferred, in a weight ratio of about 12 parts salt to 1 part indicator, since saline solutions are widely utilized in assay procedures. The procedure according to this approach is to mix the indicator and salt and then to grind the mixture in a mortar and pestle for about 10 minutes or a ball mill for about 30 minutes. The solid product is then mixed with the stabilizer and ground together as described previously. The final stabilizer indicator powder may be used in the same manner as a powder wherein no salt is used.

Acceptable results have been obtained with stabilizers having a range of molecular weight between 8,000 and 100,000 Daltons, but it is believed that higher and lower molecular weights will also produce acceptable results. Polyethylene glycol has been found to be particularly effective as a stabilizer.

In preparing an indicator solution for use in assay procedures, the stabilized indicator powder is dissolved in an aqueous medium. About 3 gm. of the powder is added to about 100 ml. of the desired aqueous medium and stirred until dissolved. This solution can be stored for up to several weeks or used immediately. By then adding the proper amount of peroxide, the solution is ready for use. Alternatively, peroxide may be added at the time the indicator solution is first prepared. Even with the addition of peroxide, the solution retains its activity with respect to peoxidase for at least several weeks.

The aqueous medium into which the stabilized powdered reagent is dissolved may be either pure water or a previously prepared solution. A solution might contain, for example, a citrate or phosphate buffer to maintain the pH of the solution, although the pH has not been found to be critical in achieving desirable results. Anionic, cationic or nonionic surfactants such as Zonyl FSA, Zonyl FSC, or Zonyl FSN (products of DuPont) may be included in the aqueous medium to assist in maintaining the oxidation products in suspension after the solution is contacted to peroxidase. The proper amount of peroxide may be added either when the aqueous medium is first prepared, immediately after the stabilized, powdered reagent is added, or at a later time prior to contacting the solution with peroxidase. The amount of peroxide is not critical but acceptable results have been achieved with a hydrogen peroxide concentration of about 0.8 mM. Further, hydrogen acceptors other than hydrogen peroxide may be utilized including, for example, methylhydroperoxide or ethylhydroperoxide.

In the presently most preferred embodiment of the invention, 4-chloro-1-naphthol is selected as the chromogenic indicator to be stabilized, inasmuch as the oxidation of this indicator produces a blue color. Most other common indicators produce a red, red-brown, or brown color, which colors are more difficult for the human eye to detect and resolve. One part of 4-chloro-1-naphthol is mixed with 250 parts of polyethylene glycol of molecular weight 8,000 Daltons using a paddle. This mixture is placed into a jar, and ceramic balls are added. The jar and its contents are refrigerated to about 4°–8° C., and then placed onto a ball mill operating at 4°–8° C. for a period of about 30 minutes, to produce the stabilized indicator powder. An indicator solution is then prepared by mixing about 3 gm. of the powder in about 100 ml. of an aqueous medium optionally containing buffers, surfactants, or peroxide. This solution may be stored in a clear bottle on a laboratory shelf for at least 2 weeks without loss of effectiveness in the peroxidase assay procedure.

The following examples, while not to be taken as limiting the invention, will illustrate aspects of the invention.

EXAMPLE 1

Two hundred mg. of 4-chloro-1-naphthol was added to 50 gm. of polyethylene glycol (8,000 m.w.). The two compounds were first mixed with a spatula, then cooled to about 4°–8° C., transferred to a ball mill and ground together for 30 minutes at about 4°–8° C. to produce a stabilized indicator powder.

EXAMPLE 2

Sixty-six mg. of 3-amino-9-ethylcarbazole was added to 10 gm. of polyethylene glycol (8,000 m.w.). The two compounds were first mixed with a spatula, and then ground together with a mortar and pestle for 10 minutes at room temperature to produce a stabilized indicator powder.

EXAMPLE 3

Fifty mg. of 4-chloro-1-naphthol was added to 10 gm. polyethylene glycol (20,000 m.w.). The two compounds were combined as in Example 2 to produce a stabilized indicator powder.

EXAMPLE 4

Fifty mg. of 4-chloro-1-naphthol was added to 10 gm. polyvinylpyrrolidone (40,000 m.w.). The two compounds were combined as in Example 2 to produce a stabilized indicator powder.

EXAMPLE 5

Fifty mg. of 4-chloro-1-naphthol was added to 10 gm. polyethyleneoxide (100,000 m.w.). The two compounds were combined as in Example 2 to produce a stabilized indicator powder.

EXAMPLE 6

Sixty-six mg. of tetramethylbenzidine was added to 10 gm. polyethylene glycol (8,000 m.w.). The two compounds were combined as in Example 2 to produce a stabilized indicator powder.

EXAMPLES 1–6 illustrate the preparation of a stabilized indicator powder in accordance with the present invention.

EXAMPLE 7

The stabilized indicator powder of EXAMPLE 1 was placed in a clear plastic bottle and stored at 37° C. for a period of 3 weeks. After storage, three grams of the indicator powder was dissolved in 100 ml. of an aqueous medium containing 0.1 ml. of 3% hydrogen peroxide. This indicator solution was then stored for an additional one-week period in a clear bottle at room temperature. No spontaneous oxidation or change in color of the stored solution was observed before, during, or after storage. After storage, the effectiveness of the solution was determined in the manner described in EXAMPLE 15. The solution was found to give acceptable results in the peroxidase assay procedure.

EXAMPLE 8

4-chloro-1-naphthol was found to be not soluble in an aqueous medium such as that described in EXAMPLE 7. To dissolve the 4-chloro-1-naphthol in aqueous solution, 0.8 grams of 4-chloro-1-naphthol was dissolved in 100 ml. of ethyl alcohol, and 2 ml. of this solution was mixed with 50 ml. of the aqueous medium described in EXAMPLE 7. This solution was stored at room temperature for one week, and it was observed visually that the solution was significantly oxidized during this one-week storage period, as evidenced by the appearance of turbidity and precipitation, and a blue-brown color. After the one-week storage period, a sample of the solution was tested in the manner of EXAMPLE 15. The results of this testing were unacceptable, inasmuch as there was little color indication due to the significant decrease of peroxidase activity. An insignificant amount of precipitated material was present on the test slide, so that color analysis was not feasible.

EXAMPLES 7 and 8 together illustrate that an unstabilized 4-chloro-1-naphthol indicator solution produces unacceptable results in a one-week storage test, but that an indicator solution prepared from 4-chloro-1-naphthol stabilized in accordance with the invention produces acceptable results in the storage test.

EXAMPLE 9

Three gm. of the stabilized indicator powder of EXAMPLE 2 was dissolved in 100 ml. of an aqueous medium containing 0.01 M citrate buffer pH 7.4. The solution was stored in a clear bottle for one week. After that period of time, the solution remained clear, indicating that no spontaneous oxidation had occurred.

EXAMPLE 10

Three gm. of the stabilized indicator powder of EXAMPLE 3 was dissolved in 100 ml. of an aqueous medium containing 0.01 M citrate buffer pH 5.3. The solution was stored in a clear bottle for one week. After that period of time, the solution remained clear, indicating that no spontaneous oxidation had occurred.

EXAMPLE 11

Three gm. of the stabilized indicator powder of EXAMPLE 4 was dissolved in 100 ml. of an aqueous medium containing 0.01 M tris buffer pH 7.0. The solution was stored in a clear bottle for one week. After that period of time, the solution remained clear, indicating that no spontaneous oxidation had occurred.

EXAMPLE 12

Three gm. of the stabilized indicator powder of EXAMPLE 5 was dissolved in 100 ml. of an aqueous medium containing 0.1 percent Zonyl FSA, an anionic surfactant. The solution was stored in a clear bottle for one week. After that period of time, the solution remained clear, indicating that no spontaneous oxidation had occurred.

EXAMPLE 13

Three gm. of the stabilized indicator powder of EXAMPLE 6 was dissolved in 100 ml. of an aqueous medium containing 0.1 percent Zonyl FSC, a cationic surfactant. The solution was stored in a clear bottle for one week. After that period of time, the solution remained clear, indicating that no spontaneous oxidation had occurred.

EXAMPLE 14

Three gm. of the stabilized indicator powder of EXAMPLE 6 was dissolved in 100 ml. of an aqueous medium containing 0.1 percent Zonyl FSN, a non-ionic surfactant. The solution was stored in a clear bottle for one week. After that period of time, the solution remained clear, indicating that no spontaneous oxidation had occurred.

EXAMPLE 15

A standard procedure was established to test the effectiveness of various solutions in detecting peroxidase activity. In this procedure, HEP-2 cells were fixed to a glass slide and contacted with a serum known to contain human antinuclear antibodies. Excess serum was washed from the slide with phosphate buffered saline solution. One drop of antihuman IgG conjugated with peroxidase was contacted to the HEP-2 cells for a period of 30 minutes, and the excess was washed off with phosphate buffered saline solution. The slide was then immersed in the indicator solution (e.g. an unstabilized solution or a stabilized solution prepared in accordance with the invention) being tested. The excess was washed away with phosphate buffered saline solution, and a cover slip was placed over the slide. The HEP-2 cells were then observed at 400X in a light microscope for the presence of color which would indicate the peroxidase reaction. Observations were made by the inventor and by an experienced medical laboratory technician.

EXAMPLE 16

As a control, the procedure of EXAMPLE 15 was followed utilizing an indicator previously utilized in the art, but not stabilized in accordance with the invention. 0.8 gm. of 4-chloro-1-naphthol was dissolved in 100 ml. of alcohol, and 2 ml. of this solution was then mixed with 100 ml. of an aqueous medium containing tris buffer pH 7.4. This solution was immediately tested by the procedure of EXAMPLE 15. A blue coloring was evident under the microscope, indicating a positive result. As another part of the control procedure, a sample of the 4-chloro-1-naphthol solution, prepared as described previously in this example, was stored at room temperature for one week. It was observed that the solution gradually became blue-brown in color and contained precipitate material, indicating spontaneous oxidation. After one week, the solution was tested by the procedure of EXAMPLE 15 and found to be ineffective in indicating the presence of peroxidase.

EXAMPLE 17

The solution of EXAMPLE 9, after one week of storage, was tested by the procedure of EXAMPLE 15, and was found to give an acceptable indication of peroxidase activity.

EXAMPLE 18

The solution of EXAMPLE 10, after one week of storage, was tested by the procedure of EXAMPLE 15, and found to give an acceptable indication of peroxidase activity.

EXAMPLE 19

The solution of EXAMPLE 11, after one week of storage, was tested by the procedure of EXAMPLE 15, and found to give an acceptable indication of peroxidase activity.

EXAMPLE 20

The solution of EXAMPLE 12, after one week of storage, was tested by the procedure of EXAMPLE 15, and found to give an acceptable indication of peroxidase activity.

EXAMPLE 21

The solution of EXAMPLE 13, after one week of storage, was tested by the procedure of EXAMPLE 15, and found to give an acceptable indication of peroxidase activity.

EXAMPLES 9–14 show that aqueous indicator solutions of the stabilized indicator powders may be readily prepared, and that such solutions are stable to spontaneous oxidation for a period of at least a week. EXAMPLES 17–21 illustrate that such solutions produce acceptable results in a peroxidase assay procedure after storage for one week. By contrast, the control test of EXAMPLE 16 illustrates that solutions prepared from unstabilized powder reagents are unstable and do not produce acceptable results after one week storage.

EXAMPLE 22

A stabilized indicator powder was prepared by first mixing a salt together with the indicator to promote uniform mixing with the indicator. 1.5 gm. of 4-chloro-1-napthol was mixed with 18.4 g. sodium chloride, and the mixture was ground in a mortar-and-pestle for 10 minutes. This mixture was mixed with 190 gm. polyethylene glycol (8000 M.W.), cooled to about 4°–8° C., and ground together in a ball mill for 1 hour at about 4°–8° C. Three gm. of the final product was dissolved in 100 ml. water and tested by the procedure of EXAMPLE 15. The stabilized indicator powder gave an acceptable indication of peroxidase activity.

Although the use of the invention is not so limited, one important approach to utilizing the stabilization and solubilization features of the present invention is through a test kit for testing for the presence of a component of a serum. In a preferred embodiment, a test kit for testing antinuclear antibodies includes glass slides with HEP-2 cells fixed thereto, a container of antihuman IgG antibodies conjugated with peroxidase enzyme, a container of a stabilized indicator powder prepared in accordance with the invention, and optionally a container of hydrogen peroxide solution and a container of an aqueous medium. (Hydrogen peroxide solution is optional in the kit as hydrogen peroxide is ordinarily readily available.) In using the test kit, the indicator powder is dissolved in water or the aqueous medium and hydrogen peroxide is added to make an indicator solution.

A test serum is contacted to the HEP-2 cells, and the excess is washed away. Then the peroxidase-conjugated antihuman IgG is contacted to the slide, and the excess is washed away. Finally, the indicator solution is contacted to the slide, and a cover slip is placed over the slide for microscopic viewing. The presence of color indicates antinuclear antibodies in the serum. This same principle may be followed in test kits wherein, for example, HEP-2 cells are replaced by other types of cells to detect other serum components. In each case, the presence of a stabilized indicator powder of the present invention increases the stability of the indicator solution and allows aqueous dissolution of the indicator without the need for organic solvents.

It may now be seen that the present invention yields a stable indicator powder for use in preparing solutions for indicating the presence of peroxidase in an assay procedure. The stabilized indicator powder may be packaged and shipped readily, and the powder is soluble in water. Thus, the user need not be concerned with providing special organic solvents for dissolving the powdered reagent prior to mixing with water, and chances of error are reduced. A solution prepared by mixing the stabilized powdered reagent in an aqueous medium is stable to spontaneous oxidation for a period of at least a week, and may be used effectively to indicate the presence of peroxidase in assay procedures. The stability of the solution obviates the need to prepare fresh solution on a daily basis, thereby avoiding the unnecessary expenditure of time and waste of valuable chemicals when excess portions of solution are discarded because they have become spontaneously oxidized and thus unreliable.

Although a particular embodiment of the invention has been described in detail for purposes of illustration, various embodiments may be made without departing from the spirit and scope of the invention. Accordingly, the invention is not to be limited accept as by the appended claims.

I claim:

1. A process for preparing a stabilized indicator powder for subsequent use in a wet chemical assay procedure, comprising the steps of:
   providing an indicator compound which is capable of being oxidized by a hydrogen acceptor in the presence of a peroxidatively active substance, the indicator compound being selected from the group consisting of 4-chloro-1-napthol, 3-amino-9-ethylcarbazole, and 3,3',5,5'-tetramethylbenzidine;
   providing a stabilizer compound selected from the group consisting of polyethylene glycol, polyethyleneoxide, polyvinylpyrrolidone, and their water soluble derivatives;
   mixing together the indicator compound and the stabilizer compound to form a solid powder mixture; and
   grinding the solid powder mixture together to form a stabilized indicator powder, whereby the indicator powder is resistant to deterioriation as a powder and also to deterioriation by spontaneous oxidation when dissolved in an aqueous solution.

2. The process of claim 1, including the further step of:
   combining the indicator compound with a salt to form a salt-combined indicator compound; said step of combining to occur after said step of providing an indicator compound and before said step of grinding.

3. A stabilized indicator powder prepared in accordance with claim 1.

4. A stabilized indicator powder prepared in accordance with claim 2.

5. A process for preparing a stabilized aqueous indicator solution for subsequent use in a wet chemical assay procedure, comprising the steps of:
   providing an indicator compound which is capable of being oxidized by a hydrogen acceptor in the presence of a peroxidatively active substance, the indicator compound being selected from the group consisting of 4-chloro-1-napthol, 3-amino-9-ethylcarbazole, and 3,3',5,5'-tetramethylbenzidine;
   providing a stabilizer compound selected from the group consisting of polyethylene glycol, polyethyleneoxide, polyvinylpyrrolidone, and their water soluble derivatives;

mixing together the indicator compound and the stabilizer compound to form a solid powder mixture;

grinding the solid powder mixture together to form a ground powder mixture; and dissolving the ground powder mixture in an aqueous medium to form a stabilized aqueous indicator solution resistant to deterioration by spontaneous oxidation.

6. The process of claim 5, including the further step of:

combining the indicator compound with a salt to form a salt-combined indicator compound; said step of combining to occur after said step of providing an indicator compound and before said step of grinding.

7. The process of claim 5, wherein the aqueous solution contains a peroxide.

8. A stablized aqueous indicator solution prepared in accordance with claim 5.

9. A stabilized aqueous indicator solution prepared in accordance with claim 6.

10. A process for preparing a stabilized aqueous indicator solution for subsequent use in assay procedures, comprising the steps of:

providing an indicator compound which is capable of being oxidized by a hydrogen acceptor in the presence of a peroxidatively active substance, the indicator compound being selected from the group consisting of 4-chloro-1-napthol, 3-amino-9-ethylcarbazole, and 3,3',5,5'-tetramethylbenzidine;

providing a stabilizer compound selected from the group consisting of polyethylene glycol, polyethyleneoxide, polyvinylpyrrolidone, and their water soluble derivatives;

mixing together the indicator compound and the stabilizer compound to form a solid powder mixture;

grinding the mixture together to form a ground powder mixture;

dissolving the ground powder mixture in an aqueous medium to form an indicator solution; and adding a peroxide to the indicator solution, the indicator solution being resistant to deterioration by spontaneous oxidation.

11. A stabilized aqueous indicator solution prepared in accordance with claim 10.

12. A process for detecting the presence of a peroxidatively active substance, comprising the steps of:

providing a sample suspected of having peroxidase activity;

providing an indicator solution containing peroxide and a dissolved stabilized indicator, the stabilized indicator having been prepared by a process including a step of grinding together an indicator compound with a stabilizer compound, the indicator compound being selected from the group consisting of 4-chloro-1-napthol, 3-amino-9-ethylcarbazole, and 3,3',5,5'-tetramethylbenzidine, and the stabilizer compound being selected from the group consisting of polyethylene glycol, polyethyleneoxide, polyvinylpyrrolidone, and their water soluble derivatives;

contacting the indicator solution to the sample; and surveying the sample for changes indicating the oxidation of the indicator.

13. A test kit for detecting the presence of a component, comprising:

(A) a test slide having attached thereto a first binding partner specific to the component;

(B) a liquid solution of a second binding partner specific to the component, said second binding partner being conjugated with a substance exhibiting peroxidase activity; and (C) a quantity of a stabilized indicator powder which is capable of being oxidized in the presence of peroxidase and a peroxide, said indicator powder being prepared by a process including a step of combining a peroxidase indicator and a stabilizer substance as set forth in claim 1.

14. The test kit of claim 13, further including:

a buffered aqueous medium for mixing with the indicator reagent powder to form a reagent solution.

15. The test kit of claim 13, wherein the first specific binding partner is HEP-2 cells.

16. The test kit of claim 13, wherein the second binding partner is antihuman IgG, and the substance exhibiting peroxidase activity is peroxidase.

17. The process of claim 13, wherein said step of combining includes the substeps of:

mixing together the indicator compound and a stabilizer substance to form a mixture; and grinding the mixture together.

18. The process of claim 1, wherein said step of grinding is performed at a temperature of from about 4 to about 8 degrees C.

19. The process of claim 2, wherein said step of grinding is performed at a temperature of from about 4 to about 8 degrees C.

20. The process of claim 5, wherein said step of grinding is performed at a temperature of from about 4 to about 8 degrees C.

21. The process of claim 10, wherein said step of grinding is performed at a temperature of from about 4 to about 8 degrees C.

22. The process of claim 12, wherein said step of grinding is performed at a temperature of from about 4 to about 8 degrees C.

23. The process of claim 5, wherein the stabilized aqueous indicator solution also contains a peroxide.

24. The process of claim 1, wherein the indicator compound is 4-chloro-napthol and the stabilizer compound is polyethylene glycol.

* * * * *